United States Patent
Guy et al.

(10) Patent No.: US 10,137,095 B2
(45) Date of Patent: *Nov. 27, 2018

(54) USE OF CANNABINOIDS IN THE TREATMENT OF EPILEPSY

(71) Applicant: GW Pharma Limited, Cambridge (GB)

(72) Inventors: Geoffrey Guy, London (GB); Stephen Wright, London (GB); Alice Mead, Cambridge (GB); Orrin Devinsky, New York, NY (US)

(73) Assignee: GW Pharma Limited, Vision Park, Histon, Cambridge ( * ) Notice: Subject to any disclaimer, the term of this patent is extended or adjusted under 35 U.S.C. 154(b) by 0 days.

This patent is subject to a terminal disclaimer.

(21) Appl. No.: 15/449,535

(22) Filed: Mar. 3, 2017

(65) Prior Publication Data

US 2017/0266126 A1 Sep. 21, 2017

Related U.S. Application Data

(63) Continuation of application No. 14/881,969, filed on Oct. 13, 2015.

(30) Foreign Application Priority Data

Oct. 14, 2014 (GB) .................................. 1418171.3

(51) Int. Cl.
| | | |
|---|---|---|
| A61K 31/05 | (2006.01) | |
| A61K 9/08 | (2006.01) | |
| A61K 31/352 | (2006.01) | |
| A61K 45/06 | (2006.01) | |
| A61K 47/10 | (2017.01) | |

(52) U.S. Cl.
CPC ............... *A61K 31/05* (2013.01); *A61K 9/08* (2013.01); *A61K 31/352* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 6,949,582 | B1 | 9/2005 | Wallace |
| 8,293,786 | B2 | 10/2012 | Stinchcomb |
| 9,017,737 | B2 | 4/2015 | Kikuchi et al. |
| 9,023,322 | B2 | 5/2015 | Van Damme et al. |
| 9,066,920 | B2 | 6/2015 | Whalley et al. |
| 9,125,859 | B2 | 9/2015 | Whalley et al. |
| 9,168,278 | B2 | 10/2015 | Guy et al. |
| 9,259,449 | B2 | 2/2016 | Raderman |
| 9,474,726 | B2 | 10/2016 | Guy et al. |
| 9,522,123 | B2 | 12/2016 | Whalley et al. |
| 9,949,936 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 2004/0110828 | A1 | 6/2004 | Chowdhury et al. |
| 2005/0266108 | A1 | 12/2005 | Flockhart et al. |
| 2006/0039959 | A1 | 2/2006 | Wessling |
| 2008/0119544 | A1 | 5/2008 | Guy et al. |
| 2008/0188461 | A1 | 8/2008 | Guan |
| 2009/0264063 | A1 | 10/2009 | Tinsley et al. |
| 2009/0306221 | A1 | 12/2009 | Guy et al. |
| 2010/0239693 | A1 | 9/2010 | Guy et al. |
| 2010/0317729 | A1 | 12/2010 | Guy et al. |
| 2011/0038958 | A1 | 2/2011 | Kikuchi et al. |
| 2011/0082195 | A1 | 4/2011 | Guy et al. |
| 2012/0004251 | A1 | 1/2012 | Whalley et al. |
| 2012/0183606 | A1 | 7/2012 | Bender et al. |
| 2012/0270845 | A1 | 10/2012 | Bannister et al. |
| 2013/0245110 | A1 | 9/2013 | Guy et al. |
| 2013/0296398 | A1 | 11/2013 | Whalley et al. |
| 2014/0100269 | A1 | 4/2014 | Goskonda et al. |
| 2014/0155456 | A9 | 6/2014 | Whalley et al. |
| 2014/0243405 | A1 | 8/2014 | Whalley et al. |
| 2014/0335208 | A1 | 11/2014 | Cawthorne et al. |
| 2014/0343044 | A1 | 11/2014 | Ceulemens et al. |
| 2015/0111939 | A1 | 4/2015 | Gruening et al. |

(Continued)

FOREIGN PATENT DOCUMENTS

| | | |
|---|---|---|
| CA | 2737447 | 10/2012 |
| CA | 2859934 | 3/2016 |

(Continued)

OTHER PUBLICATIONS

Porter et al., Report of a parent survey of cannabidiol-enriched cannabis use in pediatric treatment-resistant epilepsy, 2013, Epilepsy Behav, 29(3), pp. 574-577.*

Dulac, "Use of Lamotrigine in Lennox-Gastaut and Related Epilepsy Syndromes," J. Child Neurolog., 12(Supplement 1), S23-S29 (1997).

Dulac, "Vigabatrin in Childhood Epilepsy," J. Child Neurolog., 6(Supplement 2), S30-S37 (1991).

FDA, "Warning Letters and Test Results for Cannabidiol-Related Products," 2015 Warning Letters, Retrieved from: https://www.fda.gov/newsevents/publichealthfocus/ucm484109.htm.

(Continued)

*Primary Examiner* — Kortney L. Klinkel
*Assistant Examiner* — Tori Strong
(74) *Attorney, Agent, or Firm* — Fish & Richardson P.C.

(57) ABSTRACT

The present disclosure relates to the use of cannabidiol (CBD) for the treatment of atonic seizures. In particular the CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types. The disclosure further relates to the use of CBD in combination with one or more anti-epileptic drugs (AEDs).

8 Claims, 1 Drawing Sheet

(56) References Cited

U.S. PATENT DOCUMENTS

| | | |
|---|---|---|
| 2015/0181924 A1 | 7/2015 | Llamas |
| 2015/0320698 A1 | 11/2015 | Whalley et al. |
| 2015/0343071 A1 | 12/2015 | Vangara |
| 2015/0359756 A1 | 12/2015 | Guy et al. |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0273913 A1 | 9/2017 | Whalley et al. |
| 2018/0071210 A1 | 3/2018 | Wilkhu et al. |

FOREIGN PATENT DOCUMENTS

| | | |
|---|---|---|
| CN | 101040855 | 9/2007 |
| CN | 103110582 | 5/2013 |
| EP | 2448637 | 5/2012 |
| GB | 2384707 | 8/2003 |
| GB | 2434097 | 7/2007 |
| GB | 2434312 | 7/2007 |
| GB | 2450753 | 1/2009 |
| GB | 2009/11580 | 7/2009 |
| GB | 2456183 | 7/2009 |
| GB | 2471523 | 1/2011 |
| GB | 2478595 | 9/2011 |
| GB | 2479153 | 10/2011 |
| GB | 2471565 | 7/2012 |
| GB | 2478072 | 12/2012 |
| GB | 2478074 | 12/2012 |
| GB | 2492487 | 1/2013 |
| WO | WO 2002/064109 | 8/2002 |
| WO | WO 2003/099302 | 12/2003 |
| WO | WO 2004/016246 | 2/2004 |
| WO | WO 2004/016277 | 2/2004 |
| WO | WO 2006/054057 | 5/2006 |
| WO | WO 2006/133941 | 12/2006 |
| WO | WO 2007/083098 | 7/2007 |
| WO | WO 2007/138322 | 12/2007 |
| WO | WO 2008/094181 | 8/2008 |
| WO | WO 2008/129258 | 10/2008 |
| WO | WO 2008/146006 | 12/2008 |
| WO | WO 2009/007697 | 1/2009 |
| WO | WO 2009/007698 | 1/2009 |
| WO | WO 2009/020666 | 12/2009 |
| WO | WO 2011/001169 | 1/2011 |
| WO | WO 2011/121351 | 10/2011 |
| WO | WO 2012/033478 | 3/2012 |
| WO | WO 2012/093255 | 7/2012 |
| WO | WO 2013/032351 | 3/2013 |
| WO | WO 2015/142501 | 9/2015 |
| WO | WO 2015/184127 | 12/2015 |
| WO | WO 2015/193668 | 12/2015 |
| WO | WO 2016/022936 | 11/2016 |

OTHER PUBLICATIONS

FDA, "Warning Letters and Test Results for Cannabidiol-Related Products," 2016 Warning Letters. Retrieved from: https://www.fda.gov/newsevents/publichealthfocus/ucm484109.htm.
Guerrini et al., "Lamotrigine and Seizure Aggravation in Severe Myoclonic Epilepsy," Epilepsia, 39(5):508-512, 1998.
Martin, A.R. NIDS research monograph. (1987) vol. 79, pp. 48-58.
Miller et al., "Mapping genetic modifiers of survival in a mouse model of Dravet syndrome," Genes. Brain and Behavior (2014) 13: 163-172.
Stafstrom et al., "Models of Pediatric Epilepsies: Strategies and Opportunities," Epilepsia, vol. 47, No. 8, 2006.
Van Rijckevorsel, Neuropsychiatr Dis Treat. Dec. 2008; 4(6): 1001-1019.
Yu et al., "Reduced sodium current in GABAergic interneurons in a mouse model of severe myoclonic epilepsy in infancy," Nature Neuroscience vol. 9, No. 9 Sep. 2006 pp. 1142-1149.
U.S. Appl. No. 15/346,844, filed Nov. 9, 2016, Whalley et al.
U.S. Appl. No. 13/977,766, filed Jul. 1, 2013, Whalley et al.
U.S. Appl. No. 14/345,968, filed Mar. 20, 2014, Whalley et al.
U.S. Appl. No. 15/284,766, filed Oct. 4, 2016, Guy et al.
U.S. Appl. No. 15/449,084, filed Mar. 3, 2017, Guy et al.
U.S. Appl. No. 15/449,124, filed Mar. 3, 2017, Guy et al.
U.S. Appl. No. 15/449,185, filed Mar. 3, 2017, Guy et al.
U.S. Appl. No. 15/449,204, filed Mar. 3, 2017, Guy et al.
U.S. Appl. No. 15/449, 177, filed Mar. 3, 2017, Guy et al.
U.S. Appl. No. 14/881,954, filed Oct. 13, 2015, Guy et al.
U.S. Appl. No. 14/881,969, filed Oct. 13, 2015, Guy et al.
U.S. Appl. No. 15/449,402, filed Mar. 3, 2017, Guy et al.
U.S. Appl. No. 15/449,535, filed Mar. 3, 2017, Guy et al.
U.S. Appl. No. 14/741,829, filed Jun. 17, 2015, Guy et al.
U.S. Appl. No. 15/183,947, filed Jun. 16, 2016, Guy et al.
U.S. Appl. No. 15/519,233, filed Apr. 14, 2017, Guy et al.
U.S. Appl. No. 15/519,244, filed Apr. 14, 2017, Guy et al.
Devinsky et al., Cannabidiol: Pharmacology and potential therapeutic role in epilepsy and other neuropsychiatric disorders, 2014 *Epilepsia*, 55(6), 791-802.
International Preliminary Report on Patentability dated Sep. 1, 2017 for Application No. PCT/GB2016/051792.
Petrocellis et al., "Effects of cannabinoids and cannabinoid-enriched Cannabis extracts on TRP channels and endocamiabinoid metabolic enzymes," British Journal of Pharmacology (2011) 163 1479-1494.
ElSohly and Gul, Chapter 1. Handbook of Cannabis, ed. Roger G. Pertwee, pp. 3-22 (2014).
Etienne de Meijer, Chapter 5, Handbook of Cannabis, ed. Roger G. Pertwee, pp. 89-110 (2014).
David J. Potter, Chapter 4, Handbook of Cannabis. ed. Roger G. Pertwee, pp. 65-88 (2014).
Utah Controlled Substances Advisory Committee Meeting, Nov. 12, 2013, available at https://www.utah.gov/pmn/files/81459.pdf.
"When to Expect Results from CW Hemp Oil", downloaded Sep. 5, 2017. https://www.cwhemp.com/blog/expecting-results-from-hemp.
C.C. de Oliveira, et al., "Anticonvulsant activity of B-catyophyllene against pentylenetetrazol-induced seizures," *Epilepsy Behav.* 56:26-31(2016).
Neto, et al.. "The role of polar phytocomplexes on anticonvulsant effects of leaf extracts of Lippia Alba (Mill.) N.E. Brown chemotypes," *J. Pharm Pharmacol.* 61(7):933-9 (2009).
A. Wallace, et al.. Pediatr. Drugs, 18:197-208 (2016).
M.M. Gedde, "Clinical Experience with Cannabis in Treatment-Resistant Pediatric Epilepsy," http://www.theroc.us/images/gedde_presentation.pdf, Sep. 9-11, 2014.
E.C. Rosenberg, et al., Neurotherapeutics, 12(4): 747-768 (2015).
B.C. Kahan, et al., Trials, 16: 405 (2015).
Lieu et al., "Assessment of self-selection bias in a pediatric unilateral hearing loss study." *Otolaryngoi Head Neck Surg.* 142(3): 427-433 (2010).
Bipolar Health Group (Charlotte's Web Hemp Remedy, available online at http:/bipolarhealthgroup.org/index.php/charlottes-web-hemp-remedy/, accessed Sep. 6, 2017.
Thurstone (Avoid Charlotte's Web for Epilepsy available online at http://drthurstone.com/charlotted-web-not-safest-option-epiliepsy-treatment/, published Jun. 26, 2014.
[No Author Listed] "Cannabidiol for Aicardi Syndrome," *Salutaris.*, Retrieved on Feb. 10, 2017, Retrieved from the internet: URL http://web.archive.org/web/20141012220050/http://salutarisdrops.com/cannabidiol-aicardi-syndrome/, © 2014, 3 pages.
[No Author Listed] "Cannabidiol Therapy for Aicardi Syndrome" Aug. 2014, 4 pages.
[No Author Listed] "Cannabinoid," *Wikipedia.*, Retrieved on Mar. 1, 2017, Retrieved from Internet: URL https://en.wikipedia.org/wiki/Cannabinoid, 15 pages.

(56) References Cited

OTHER PUBLICATIONS

[No Author Listed] "Convulsive Disorders and Their Interference with Driving," *Medicos.*, Retrieved Feb. 10, 2017, Retrieved from internet: URL https://www.medicosporlaseguridadvial.com/en/clinical-subjects/neurologic-diseases/convulsive-disorders-and-their-interference-with-driving/, 2014, 3 pages.

[No Author Listed] "Estimating the maximum Safe Starting Dose in Initial Clinical Trials for Therapeutics in Adult Healthy Volunteers," *FDA Guidance for Industry.*, Jul. 2005, 30 pages.

[No Author Listed] "GW Pharmaceuticals Announces Epidiolex(R) Receives Fast Track Designation from FDA for the Treatment of Dravet Syndrome," *GW Pharmaceuticals Press Release.*, dated Jun. 6, 2014.

[No Author Listed] "GW Pharmaceuticals Announces Physician Reports of Epidiolex(R) Treatment Effect in Children and Young Adults with Treatment-resistant epilepsy from Physician-Led Expanded Access Treatment Program," *GW Pharmaceuticals Press Release.*, dated Jun. 17, 2014.

[No Author Listed] "GW Pharmaceuticals Provides Update on Orphan Program in Childhood Epilepsy for Epidiolex ®," *GW Pharm.*, Available online Nov. 14, 2013, Retrieved Feb. 10, 2017, Retrieved from the internet: URL http://www.gwpharm.com/GW%20Phannaceuticals%20Provides%20Update%20on%20Orphan%20Program%20childhood%20EPilepsy%20for%20Epidiolex.aspx, 5 pages.

[No Author Listed] "GW Pharmaceuticals Receives Orphan Drug Designation by FDA for Epidiolex® in the Treatment of Lennox-Gastaut Syndrome," *GW Pharm.*, Available online Feb. 28, 2014, Retrieved Feb. 10, 2017, Retrieved from the internet: URL https://www.gwpharm.com/about-us/news/gw-pharmaceuticals-receives-orphan-drug-designation-fda-epidiolex%C2%AE-treatment-lennox, 4 pages.

[No Author Listed] "Orphan Drug Designation Granted for Epidiolex in Dravet syndrome by the FDA-Seven Expanded Access INDs granted by FDA to US physicians to treat with Epidiolex 125 children suffering from intractable epilepsy syndromes," *GW Pharmaceuticals Press Release.*, dated Nov. 14, 2013, 3 pages.

[No Author Listed] "What are the Highest CBD Strains?" accessed Feb. 16, 2017, available online at www.leafscience.com, published Oct. 15, 2014, 2 pages.

Alger, "Not Too Excited? Thank Your Endocannabinoids," *Neuron.*, 51(4):393-395, Aug. 17, 2006.

Ames et al., "Anticonvulsant effect of cannabidiol," *S. Mr Med. J.*, 69(1):14, Jan. 4, 1986.

Annex to the Communication-Opposition for Application No. 10734541.5, dated Jan. 28, 2016, 5 pages.

Arain et al., "Pregabalin in the Management of Partial Epilepsy," *Neuropsychiatr Dis Treat.*, 5:407-413. Epub Aug. 20, 2009.

Avoli et al., "Cellular and molecular mechanisms of epilepsy in the human brain," *Prog Neurobiol.*, 77(3):166-200, 2005.

Bakhsm, Miftaah-al-Khazaain 1930: 607-8. Urdu. Exhibit 3.

Bancaud et al., "Proposal for Revised Clinical and Electroencephalographic Classification of Epileptic Seizures," *Epilepsia.*, 22(4):489-501, Aug. 1981.

Benowitz et al., "Metabolic and Psychophysiologic studies of cannabidiol hexobarbital interaction," *Clin Pharmacol Ther.*, 28(1):115-120, 1980.

Bhatt et al., "Indigenous Plants in Traditional Healthcare System in Kedarnath Valley of Western Himalaya," *Indian J Tradit Knowl.*, 7(2):300-310, Apr. 2008.

Bhattacharyya et al., "Modulation of mediotemporal and ventrostriatal function in humans by Delta9-tetrahydrocannabinol: a neural basis for the effects of Cannabis sativa on learning and psychosis," *Arch Gen Psychiatry.*, 66:442-451, 2009.

Booth et al., "Legalization's opening of medical pot research is dream and nightmare," *Denver Post*, Dec. 14, 2013.

Bostanci et al., "The effects of octanol on penicillin induced epileptiform activity in rats: An in vivo study," *Epilepsy Res.*, 71(2-3):188-194, Jul. 27, 2006.

Braida et al., "Post-ischemic treatment with cannabidiol prevents electroencephalographic flattening, hyperlocomotion and neuronal injury in gerbils" *Neuroscience Letters.*, 346:61-64, 2003.

Brust et al., "Marijuana use and the risk of new onset seizures," *Trans Am Clin Climatol Assoc.*, 103:176-181, 1992.

Carlini et al., "Hypnotic and Antiepileptic Effects of Cannabidiol," *J Clin Pharmacol.*, 21(8-9 Suppl):417S-427S. Aug.-Sep. 1981 Abstract only.

Castel-Branco et al., "The Maximal Electroshock Seizure (MES) Model in the Preclinical Assessment of poetential New Antiepileptic Drugs," *Methods Find Exp Clin Pharmacol.*, 31(2); 101-106, 2009.

Catherine Jacobson et al: "Survey of Current Cannabidiol Use in Pediatric Treatment-Resistant Epilepsy", Apr. 22, 2013 (Apr. 22, 2013), XP055238831, Retrieved from the Internet:URL:https://www.thcint.com/uploads/1/9/3/7/19371199/cannabidiol_use_in_pediatric_epilepsy.pdf.

Chiron, C. et al. *Epilepsia*, 2011, vol. 52 Suppl. 2, pp. 72-75.

Chiu et al., "The Influence of Cannabidiol and Δ9-Tetrahydrocannabinol on Cobalt Epilepsy in Rats," *Epilepsia.*, 20:365-375, 1979.

Combined Search and Examination Report dated Jan. 4, 2012 for Application No. GB1116789.7.

Combined Search and Examination Report dated Mar. 25, 2011 for Application No. GB1100043.7.

Combined Search and Examination Report dated Sep. 5, 2014 for Application No. GB1414813.4.

Combined Search and Examination Report under Sections 17 and 18(3) for International Application No. GB1121919.3, dated Feb. 29, 2012, 8 pages.

Combined Search and Examination Report under Sections 17 and 18(3) for International Application No. GB1410771.8, dated Feb. 27, 2015, 7 pages.

Combined Search and Examination Report under Sections 17 and 18(3) for International Application No. GB1418166.3, dated Jul. 2, 2015, 8 pages.

Combined Search and Examination Report under Sections 17 and 18(3) for International Application No. GB1418170.5, dated Jul. 2, 2015, 6 pages.

Combined Search and Examination Report under Sections 17 and 18(3) for International Application No. GB1418171.3, dated Jun. 29, 2015, 8 pages.

Combined Search and Examination Report under Sections 17 and 18(3) for International Application No. GB1506550.1, dated Feb. 5, 2016, 9 pages.

Communication of a Notice of Opposition for Application No. 10734541.5, dated Dec. 17, 2014, 1 page.

Communication Pursuant to Artilce 94(3) EPC in European Patent Application No. 10734541.5, dated Oct. 23, 2012, 3 pages.

Consroe et al., "Anticonvulsant drug antagonism of Δ9 tetrahydrocannabinol-induced seizuers in rabbits," *Res Commun Chem Pathol Pharmacol.*, 16(1):1-13, Jan. 1977.

Consroe et al., "Anticonvulsant Interaction of Cannabidiol and Ethosuximide in Rats," *J. Pharm. Pharmac.*, 29(8):500-501, Aug. 1977.

Consroe et al., "Anticonvulsant Nature of Marihuana Smoking," *JAMA.*, 234(3):306-307, Oct. 20, 1975.

Consroe et al., "Cannabidiol—Antiepileptic Drug Comparisons and Interactions in Experimentally Induced Seizures in Rats," *J. Pharm. Exp. Therap.*, 201(1):26-32, Apr. 1977.

Consroe et al., "Effects of Cannabidiol on Behavioral Seizures Caused by Convulsant Drugs or Current in Mice," 83(3-4):293-298, Sep. 24, 1982.

Consroe et al., "Therapeutic Potential of Cannabinoids in Neurological Disorders," Chapter 2, pp. 21-49, Cannabinoids as Therapeutic Agents, R. Mechoulam, ed., CRC Press, Boca Raton (1986).

Consroe et al., Chapter 12, "Potential Role of Cannabinoids for Therapy of Neurological Disorders," p. 459 in Marijuana/Cannabinoids: Neurobiology and Neurophysiology, ed. L. Murphy (1992).

Cortesi et al., "Potential therapeutical effects of cannabidiol in children with pharmacoresistant epilepsy," *Med Hypotheses.*, 68(4):920-921, 2007.

(56) References Cited

OTHER PUBLICATIONS

Cortez et al., Chapter 10 "Pharmacologic Models of Generalized Absence Seizures in Rodents," *Models Seizures Epilepsy.*, 111-126, 2006.
Cunha et al., "Chronic Administration of Cannabidiol to Healthy Volunteers and Epileptic Patients," Pharmacology., 21(3):175-185 (1980).
Czapinski et al., "3-17-08 Randomized 36-month comparative study of valproic acid (VPA), phenytoin (PHT), phenobarbital (PB) and carbamazepine (CBZ) efficacy in patients with newly diagnosed epilepsy with partial complex seizures," *J. Neurol. Sci.*, 150(1):S162-S163, Sep. 1997.
Dasa et al., Brhat Nighantu Ratnakara (Saligramanighantubhusanam). vol. IV. 1997:170. Sanskrit. Exhibit 5.
Davis et al., "A Predominant Role for Inhibition of the Adenylate Cyclase/Protein Kinase A Pathway in ERK Activation by Cannabinoid Receptor 1 in NIE-115 Neuroblastoma Cells," *J Biol Chem.*, 278(49):48973-80, Dec. 5, 2003.
Davis et al., "Antiepileptic action of marijuana-active substances," *Federation Proceedings.*, 8:284-285, 1949.
Decision in Opposition proceedings (Art. 101(3)(a) and 106(2) EPC in European Patent Application No. EP2448637, dated Dec. 15, 2016, 91 pages.
Declaration of Professor Anthony G. Marson in the Inter Partes Review of U.S. Pat. No. 9,066,920, dated Dec. 13, 2016, 28 pages.
Declaration of Professor Leslie Benet in the Inter Partes Review of U.S. Pat. No. 9,066,920, dated Nov. 22, 2016, 18 pages.
Deshpande et al., Cannabinoid CBI Receptor Antagonists Cause Status Epilepticus-like Activity in the Hippocampal Neuronal Culture Model of Acquired Epilepsy, *Neurosci Lett.*, 411(1):11-6, Jan. 2007.
Dravet, "The core Dravet syndrome phenotype," *Epilepsia.*, 52 Suppl 2:3-9, Apr. 2011.
Dreifus et al., "Proposal for Revised Clinical and Electroencephalographic Classification of Epileptic Seizures," *Epilepsie.*, 22:489-501, 1981.
Drugs of the Future, 39(1): 49-56, Jan. 2014 notes Orphan Drug designation for CBD for Lennox-Gastaut Syndrome.
Eadie, "Shortcomings in the current treatment of epilepsy," *Expert Rev Neurother.*, 12(12):1419-1427, Dec. 2012.
Eggers, "Temporal lobe epilepsy is a disease of faulty neuronal resonators rather than oscillators, and all seizures are provoked, usually by stress," *Med Hypotheses.*, 69(6): 1284-9, 2007.
Engel et al., Chapter 1, "What Should be Modeled," In *Models Seizure Epilepsy.*, 2006, 14 pages.
Engel, "Report of the ILAE Classification Core Group," *Epilepsia.*, 47(9):1558-1568, 2006.
Examination Report dated Mar. 18, 2014 for Application No. GB1100043.7.
Fariello, "Parenteral Penicillin in Rats: An Experimental Model of Multifocal Epilepsy," *Epilepsia*, 17:217-222, 1976.
Ferdinand et al., "Cannabis—Psychosis Pathway Independent of Other Types of Psychopathology," *Schizophrenia Research.*, 79:289-295, 2005.
Fisher et al., "The impact of epilepsy from the patient's perspective I. Descriptions and subjective perceptions," *Epilepsy Research.*, 41(1):39-51, 2000.
Gabor et al., "Lorazepam Versus Phenobarbital: Candidates for Drug of Choice for Treatment of Status Epilepticus," *J Epilepsy.*, 3(1):3-6, Jan. 1990.
Gallily et al., "Overcoming the Bell-Shaped Dose-Response of Cannabidiol by Using Cannabis Extract Enriched in Cannabidiol," *Pharmacology & Pharmacy.*, 6:75■85, Jan. 2015.
Gastaut., "Clinical and Electroencephalographical Classification of Epileptic Seizures," *Epilepsia.*, 11:102-113, 1970.
Gedde, M. et al Epilepsey Currents 2014 Posters excerpt pp. 449-450.
Geffrey et al., "Cannabidiol (CBD) Treatment for Refractory Epilepsy in Tuberous Sclerosis Complex (TSC)," *American Epilepsy Society.*, Annual Meeting Abstracts: View, Abstract 2.427, 2014, retrieved on Feb. 10, 2017, retrieved from the internet: URL <https://www.aesnet.org/meetings_events/annual_meeting_abstracts/view/1868979>, 2 pages.
Green, "CBD: An Unconventional Therapy," available online at http://nugs.com/article/cbd-an-unconventional-therapy.html, published Mar. 24, 2014, 5 pages.
Gresham et al., "Treating Lennox-Gastaut syndrome in epileptic pediatric patients with thirdgeneration rufinamide," *Neuropsychiatr Dis Treat.*, 6:639-645, Oct. 5, 2010.
Gross et al., "Marijuana use and Epilepsy: Prevalence in Patients of a Tertiary Care Epilepsy Center," *Neurology.*, 62(11):2095-7, Jun. 8, 2004.
Guimaraes et al., "Antianxiety effect of cannabidiol in the elevated plus-maze," *Psychopharmacology.*, 100:558-559, 1990.
Heinemann et al., "An Overview of In Vitro Seizure Models in Acute and Organotypic Slices," Chapter 4, 35-44, 2006.
Hill et al., "A■-Tetrahydrocannabivarin suppresses in vitro epileptiform and in vivo seizure activity in adult rats," *Epilepsia.*, 51(8):1522-1532, Aug. 2010.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," *ACS Chem. Neurosci.*, 5:1131-1141, Jul. 16, 2014.
International Preliminary Report on Patentability in International Application No. PCT/GB2010/051066, dated May 3, 2011, 6 pages.
International Preliminary Report on Patentability dated Apr. 18, 2017 for Application No. PCT/GB2015/053030.
International Preliminary Report on Patentability dated Dec. 12, 2013 for Application No. PCT/GB2012/052284.
International Preliminary Report on Patentability dated Jun. 9, 2011 for Application No. PCT/GB2010/051066.
International Search Report and Written Opinion dated Aug. 25, 2015 for Application No. PCT/GB2015/051776.
International Search Report and Written Opinion dated Aug. 26, 2015 for Application No. PCT/GB2015/051775.
International Search Report and Written Opinion dated Dec. 13, 2010 for Application No. PCT/GB2010/051066.
International Search Report and Written Opinion dated May 30, 2011 for Application No. PCT/GB2011/050649.
International Search Report and Written Opinion dated Nov. 16, 2012 for Application No. PCT/GB2012/052284.
International Search Report in International Application No. PCT/GB2010/051066, dated Nov. 16, 2010, 3 Pages.
International Search Report in International Application No. PCT/GB2012/050002, dated Feb. 24, 2012, pages.
Iuvone et al., "Neuroprotective Effect of Cannabidiol, a Nonpsychoactive Component From Cannabis Sativa, on Beta-amyloid-induced toxicity in PC12 Cells," *J Neurochem.*, 89(1):134-41, Apr. 2004.
Izzo et al., "Non-psychotropic plant cannabinoids: new therapeutic opportunities from an ancient herb," *Trends in Pharmacological Sciences.*, 30(10):515-527, 2009.
Jeavons et al., "Sodium Calproate in Treatment of Epilepsy," *Br Med J.*, 2(5919):584-6, Jun. 15, 1974.
Jones, et al., "Cannabidiol Displays Antiepileptiform and Antiseizure Properties in Vitro and in Vivo," *J. Pharmacol Exp Ther.*, 332(2):559-577, Feb. 2010.
Joy et al., "Marijuana and Medicine Assessing the Science Base", *Instit Med.*, National Academy Press, p. 125, 170 pages total, 1999.
Karler et al., "The Cannabinoids as Potential Antiepileptics," *J Clin Pharmacol.*, 21:437S-448S, Aug.-Sep. 1981.
Khan et al., Khazaain-al-Adiva. vol. I. 1911:885. Urdu. Exhibit 7.
Khan et al., Khazaain-al-Adiva. vol. I. 1911:886. Urdu. Exhibit 4.
Khan et al., Khazaain-al-Advia, vol. I. 1911: 889. Urdu. Exhibit 3.
Khan et al., Khazaain-al-Advia, vol. I. 1911: 889. Urdu. Exhibit 4.
Khan et al., Muheet-e-Azam, vol. II. 1887: 147. Persian. Exhibit 1.
Klitgaard et al., "Electrophysiological, neurochemical and regional effects of levetiracetam in the rat pilocarpine model of temporal lobe epilepsy," *Seizure.*, 12(2):92-100, Mar. 2003.
Kramer et al., "Febrile infection-related epilepsy syndrome (FIRES): pathogenesis, treatment, and outcome: a multicenter study on 77 children," *Epilepsia.*, 52(11):1956-65, Nov. 2011.

(56) References Cited

OTHER PUBLICATIONS

Kwan et al., Definition of drug resistant epilepsy: consensus proposal by the ad hoc Task Force of the ILAE Commission on Therapeutic Strategies. *Epilepsia.*, 51(6):1069-77, Jun. 2010 Erratum in: Epilepsia. 51(9): 1922, Sep. 2010.
Letter from Opponenet Rregarding Oral Proceedings in European Patent No. EP2448637, dated Oct. 20, 2016, 6 pages.
Lindamood et al., "Effects of Δ9-Tetrahydrocannabinol and Cannabidiol on Sodium-Dependent High Affinity Choline Uptake in the Rat Hippocampus1," *J Pharmacology Experimental Therapeutics.*, 213(2):216-221, 1980.
Long et al., "The Pharmacological actions of cannabidiol," *Drugs of the Future.*, 30(7), 747-753, Jul. 1, 2005.
Lowenstein D.H., Chapter 363, Section 2 "Diseases of the Central Nervous System," *Seizures and Epilepsy.*, 2498-2512, 2008.
Luttjohann et al., "A Revised Racine's scale for PTZ-induced seizures in rats," *Physiology & Behavior.*, 98:579-586, 2009.
Lutz., "On-demand activation of the endocannabinoid system in the control of neuronal excitability and epileptiform seizures," *Biochemical Pharmacology*, 68(9):1691-1698, Nov. 2004.
Maa et al., "The Case for Medical Marijuana in Epilepsy," *Epilepsia.*, 55(6):783-786, Jun. 2014.
Mackie., "Cannabinoid Receptors as Therapeutic Targets," *Annu Rev Pharmacol Toxicol.*, 46:101-122, 2006.
Majoosi, et al. Kaamil-al-Sena'ah, Part II, Central Council for Research in Unani Medicine. 2005: 116. Arabic. Exhibit 2.
Malfait et al., "The nonpsychoactive cannabis constituent cannabidiol is an oral anti-arthritic therapeutic in murine collagen-induced arthritis," *PNAS.*, 97(17):9561-9566, Aug. 15, 2000.
Mattson et al., "Comparison of carbamazepine, phenobarbital, phenytoin, and primidone in partial and secondarily generalized tonic-clonic seizures," *N Engl J Med.*, 313(3):145-151, Jul. 18, 1985.
Mattson et al., "Prognosis for total control of complex partial and secondary generalized tonic clonic seizures," *Neurology.*, 47:68-76, 1996.
McCormick et al., "On the Cellular Network Bases of Epileptic Seizures," *Annu Rev Physiol.*, 63:815-846, 2001.
Mechoulam et al., "Cannabidiol: An Overview of Some Pharmacological Aspects," *J Clin Pharmacol.*, 42:11S-19S, 2002.
Mechoulam et al., "Toward drugs derived from cannabis," *Naturwissenschaften.*, 65(4): 174-179, Apr. 1978.
Merlis., "Proposal for an International Classification of the Epilepsies," *Epilepsia.*, 11:114-119, 1970.
Models of Chemically-Induced Acute Seizures 127-152, 2006.
Morad et al., "Conversion to Sirolimus-Based Immunosuppression in Maintenance Liver Transplantation Patients," *Liver Transplantation.*, 13:658-664, 2007.
Ng et al., "Illicit Drug Use and the Risk of New-Onset Seizures," *Am J Epidemiol.*, 132(1):47-57, 1990.
Notice of Allowance in U.S. Appl. No. 13/380,305, dated Dec. 10, 2014, 5 pages.
Notice of Allowance in U.S. Appl. No. 13/380,305, dated Mar. 19, 2015, 7 pages.
Notice of Appeal in European Patent No. EP2448637, dated Feb. 14, 2017, 5 pages.
Notice of Opposition to a European Patent No. EP2448637, dated Dec. 5, 2014, 20 pages.
Obay et al., "Antiepileptic effects of ghrelin on pentylenetetrazole-induced seizures in rats," *Peptides.*, 28(6):1214-1219, Jun. 2007.
Office Action in U.S. Appl. No. 13/380,305, dated Aug. 25, 2014.
Opponent Response to the Preliminary Opinion of the Opposition Division in European Patent No. EP2448637, dated Jun. 23, 2016, 27 pages.
Opponent Response to the Preliminary Opinion of the Opposition Division in European Patent No. EP2448637, dated Sep. 9, 2016, 25 pages.
Opponent Response to the Written Submissions in European Patent No. EP2448637, dated Oct. 12, 2016, 18 pages.
Opponent Response to the Written Submissions in European Patent No. EP2448637, dated Oct. 20, 2016, 3 pages.
Opponent Written Submission in European Patent No. EP2448637, dated Nov. 4, 2016, 3 pages.
Pelliccia et al., "Treatment with CBD in oily solution of drug-resistant paediatric epilepsies," Available online Sep. 2, 2010, Retrieved Jun. 30, 2015, Retrieved from the internet: URL http://www.cannabis-med.org/studies/ww_en_db_study_show.php?s_id=173&&search_pattern=Epilepsy, 2 pages, Abstract only.
Pereira et al., Study pharmacologic of the GABAergic and glutamatergic drugs on seizures and status epilepticus induced by pilocarpine in adult Wistar rats, *Neurosci Lett.*, 419(3):253-7, Jun. 4, 2007.
Pertwee, "Cannabinoid receptor ligands: clinical and neuropharmacological considerations, relevant to future drug discovery and development," *Expert Opin Investig Drugs.*, 9(7): 1553-71, Jul. 2000.
Pertwee, "The diverse CB1 and CB2 receptor pharmacology of three plant cannabinoids: Δ9- tetrahydrocannabinol, cannabidiol and Δ9-tetrahydrocannabivarin," *Br. J. Pharmacol.*, 153(2):199-215, 2008.
Pertwee, Chapter 3, "The Pharmacology and Therapeutic Potential of Cannabidiol," pp. 32-83 in the book Neuroscience Intelligence Unit: Cannabinoids, Ed Vincenzo Di Marzo, Springer Science & Business Media, (2004).
Petition for Inter Partes Review of U.S. Pat. No. 9,066,920, dated Dec. 16, 2016, 77 pages.
Pohl et al., "Effects of flunarizine on Metrazol-induced seizures in developing rats," *Epilepsy Res.*, 1:302-305, 1987.
Porter et al., "Report of a Parent Survey of Cannabidiol-enriched Cannabis use in Pediatric Treatment-resistant Epilepsy," *Epilepsy Behavior.*, 29(3):574-577, Dec. 2013.
Press et al., "Parental reporting of response to oral cannabis extracts for treatment of refractory epilepsy," *Epilepsy Behav.*, 45:49-52, Apr. 2015.
Rauca et al., "The role of superoxide dismutase and a-tocopherol in the development of seizures and kindling induced by pentylenetetrazol—influence of the radical scavenger a-phenyl-N-tert-butyl nitrone," *Brain Research.*, 1009(1-2):203-212, May 29, 2004.
Russo, Taming THC: potential cannabis synergy and phytocannabinoid-terpenoid entourage effects, 163 British J. of Pharm. 1333 (2011).
Reply of the Patent Proprietor to the Notice(s) of Opposition in European Patent No. 2448637, dated May 28, 2015, 12 pages.
Reply to Communication from the Examining Division in European Patent Application No. 10734541.5, dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016 13 pages.
Reply to Opponent's Written Submissions in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in U.S. Appl. No. 13/380,305, filed Mar. 2, 2015, 3 pages.
Resstel et al., "5-HT1A receptors are involved in the cannabidiol-induced attenuation of behavioural and cardiovascular responses to acute restraint stress in rats," *Br J Pharmacol.*, 156(1): 181-8, Jan. 2009.
Rubio et al., "In Vivo Experimental Models of Epilepsy," *Central Nervous System Agents in Medicinal Chemistry.*, 10:298-309, 2010.
Sadanandasarma et al., Rasatarangini I Ith Ed. 1979:720-3. Sanskrit. Exhibit 6.
Sander., "The epidemiology of epilepsy revisited," *Curr Opin Neurol.*, 16(2):165-170, Apr. 2003.
Sastri et al., Anandakandam. 1st Edition. 1952:241. Sanskrit. Exhibit 2.
Scuderi et al., "Cannabidiol in Medicine: A Review of its Therapeutic Potential in CNS Disorders," *Phytother Res.*, 23(5):597-602, May 2009.
Silva, R. et al., Can. J. Neurol. Sci. 2006 vol. 33 pp. 783-786.
Statement of Opposition for EP10734541.5 dated Dec. 5, 2014.
Stott et al., "Cannabinoids for the pharmaceutical industry," *Euphytica.*, 140:83-93, 2004.

(56) References Cited

OTHER PUBLICATIONS

Swann., "The Effects of Seizures on the Connectivity and Circuitry of the Developing Brain," *MRDD.*, 10(2):96-100, 2004.
Third Party Observations for Application No. AU2012314128 dated Mar. 19, 2015.
Third Party Observations for Application No. EP1 1712658.1 dated Nov. 22, 2013.
Third Preliminary Amendment under 37 C.F.R. 1.115 in U.S. Appl. No. 13/380,305, dated May 23, 2014, 4 pages.
Thomas et al., "Evidence that the Plant Cannabinoid Δ9-Tetrahydrocannabivarin is a Cannabinoid CBI and CB2 Receptor antagonist," *Br J Pharmacol.*, 146(7):917-926, Dec. 2005.
Thurman et al., "Standards for epidemiologic studies and surveillance of epilepsy," *Epilepsia.*, 52 Suppl 7:2-26, Sep. 2011.
Trembly et al., "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract Only.
Turkanis et al., "An Electrophysiological Analysis of the Anticonvulsant Action of Cannabidiol on Limbic Seizures in Conscious Rats," *Epilepsia.*, 20:351-363, 1979.
Usami et al., "Synthesis and Pharmacological Evaluation in Mice of Halogenated Cannabidiol Derivatives," *Chem Pharm Bull.*, 47(11):1641-1645, Nov. 1999.
Velisek., "Models of Chemically-Induced Acute Seizures," *Models Seizure Epilepsy.*, 127-152, 2006.
Veliskova., Chapter 48 "Behavioral Characterization of Seizures in Rates," *Models Seizures Epilepsy.*, 601-611, 2006.
Vollner et al., Haschisch XX: Cannabidivarin, ein neuer Haschisch-Inhaltsstoff, *Tetrahedron Lett.*, 10(3):145-147, 1969.
Wahle et al., "Development of Tolerance to the Anticonvulsant Effect of Valproate but not to Ethosuximide in a Rat Model of Absence Epilepsy," *Eur J Pharma.*, 181(1-2):1-8, May 1990.
Wallace et al., "Assessment of the role of CB1 receptors in cannabinoid anticonvulsant effects," *European J Pharmacology.*, 428(1):51-57, 2001.
Weston et al., "Tetrahydrocannabivarin Exhibits Anticonvulsant Effects in a Piriform Cortical Brain Slice Model of Epileptiform Activity," *Pro British Pharm Soc.*, Retrieved on Mar. 1, 2017, Retrieved Online: URL http://www.pA2online.org/abstract/abstract.jsp?abid=28533, 1 page, Abstract Only.
Whole-Plant Cannabinoids Outperform Single Molecule Compounds at 1/5, Charlotte's Web: by the Stanley Brothers (Jan. 11, 2017) available at https://www.cwhemp.com/blog/whole-plant-cw-hemp-cannabinoids.
Wingerchuk., "Cannabis for medical purposes: cultivating science, weeding out the fiction," *Lancent.*, 364:315-316, Jul. 24, 2004.
Written Opinion of the International Application No. PCT/GB2010/0051066, dated Nov. 22, 2010, 4 pages.
Yuriev, "Endogenic Cannabinoid System is a New Perspective Object of Pharmacotherapeutic Effect to Disease of Nervous System," *Ukrainskv Metodichny Chasopis*, 6(50): 21-9, 2005.
Zhao et al., Chapter 27 "Repetitive Seizures in the Immature Brain," *Models Seizures Epilepsy.*, 341-350, 2006.
Zuardi et al., "Cannabidiol, a Cannabis sativa constituent, as an antipsychotic drug," *Brazilian Journal of Medicine and Biological Research.*, 39(4): 421-429, Apr. 2006.
Zuardi et al., "Cannabidiol: from an inactive cannabinoid to a drug with wide spectrum of action," *Rev Bras Psiquiatr.*, 30(3): 271-80 (2008).
Supplemental Expert Statement of Professor Benjamin J Whalley, dated Nov. 4, 2016, 9 pages.
Expert Statement of Vincenzo Di Marzo for Application No. EP10734541.5, dated Sep. 9, 2016.
Expert Statement of Professor Benjamin J. Whalley for Application No. EP10734541.5, dated Sep. 9, 2016.
Expert Statement of Dr. Emma Louise Cheetham, dated Nov. 4, 2016, 6 pages.
Third Party Observations for Application No. EP10734541.5 dated Apr. 3, 2017.

Holmes et al. "Choosing the Correct AED: From Animal Studies to the Clinic," *Pediatr Neurol.* Mar. 2008; 38(3): 151-162.
Statement of Grounds of Appeal for European Application No. 10734541.5 in the name of GW Pharma and Otsuka Pharmaceutical Co. Limited Appellant/Opponent: Insys Therapeutics Inc., dated Apr. 21, 2017.
Statement of Grounds of Appeal for European Application No. 10734541.5 on behalf of the Proprietors: GW Pharma Limited and Otsuka Pharmaceutical CO Limited, dated Apr. 12, 2017.
Patent Owners' Preliminary Response for IPR2017-00503 dated Apr. 11, 2017, 45 pages.
Decision in IPR2017-00503 dated Jul. 7, 2017, 26 pages.
Mares et al., Electrical Stimulation-Induced Models of Seizures in Model of Seizures and Epilepsy (Asla Pitkänen, Philip A. Schwartzkroin & Solomon L. Moshé, eds.), 2004.
American Epilepsy Society, Three Studies Shed New Light on the Effectiveness of Cannabis in Epilepsy, Oct. 14, 2014 (Year:2014).
Barker-Haliski et al, How Clinical Development Can, and Should inform Translational Science, Neuron 84, Nov. 5, 2014.
Bertram, "The Relevance of Kindling for Human Epilepsy," Apr. 1, 2007, 48(s2):65-74.
Conry et al. Epilepsia 2009, 50, 1158-1166 (2009).
Declaration of Professor H. Steve White In the Inter Panes Review of U.S. Pat. No. 9,066,920, dated Oct. 24, 2017, 69 pages.
Ex parte Edelstam, Appeal No. 2016/006358, dated Jun. 21, 2017 (Year: 2017).
Ex parte Miller, Appeal 2009-011751, dated Jul. 8, 2010 (Year: 2010).
Goodman & Gilman, The Pharmacological Basis of Therapeutics (Brunton, Laurence L.; Lazo, John S.; Parker, Keith, eds. (2006); (11th ed.), New York: McGraw-Hill. ISBN 0-07-142280-3); Chapter 19, Pharmacotherapy of the Epilepsies.
ICE Epilepsy Alliance, The Dravet Syndrome Spectrum, Nov. 2008 (Year: 2008).
Klitgaard H, Matagne A, Gobert J, Wülfert E. "Evidence for a unique profile of levetiracetam in rodent models of seizures and epilepsy." European journal of pharmacology. Jul. 24, 1998, 353(2):191-206.
Löscher W, Schmidt D. "Modern antiepileptic drug development has failed to deliver: ways out of the current dilemma." Epilepsia. Apr. 1, 2011, 52(4):657-78.
Marino, "Status Epilepticus: Current Treatment Strategics," The Neurohospitalist. Jan. 2011, 1(1):23-31.
Oakley, et al., "Dravet Syndrome Insights into pathophysiology and therapy from a mouse model of Dravet syndrome," Epilepsia, 52(Suppl. 2):59-61 (2011).
Petitioner's Reply to Patent Owner's Response in Inter Panes Review No. IPR20117-00503, filed Jan. 19, 2018, 36 pages.
Sperling et al., "Carisbamate as adjunctive treatment of partial onset seizures in adults in two randomized, placebo-controlled trials," Epilepsia Mar. 2010;51(3):333-43.
Tanya Lewis, Mystery Mechanisms, The Scientist Magazine, Jul. 29, 2016, 2 pages.
Transcript of Dr. H. Steven White's deposition, dated Dec. 29, 2017, 50 pages.
Arslan and Tirnaksiz, "Self-emulsifying Drug Delivery Systems," Fabad J Pharm Sci, 2013,38(1): 55-64.
ChildNeurologyFoundation.org [online], "Disorder Directory: Learn from the Experts—LGS (Lennon-Gastaut Syndrome)," Child Neurology Foundation, available on or before Sep. 6, 2005, retrived on May 21, 2018, URL http://www.childneurologyfoundation.org/disorders/lgs-lennox-gastaut-syndrome, 10 pages.
EPO Opposition, Expert Statement of Professor Anthony G Marson in European Appln. No. EP10734541.5 , dated Jun. 14, 2016, 9 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.

(56) References Cited

OTHER PUBLICATIONS

GB Combined Search and Examination Report in Application No. GB1611544.6, dated Mar. 29, 2017, 8 pages.
GB Combined Search and Examination Report in GB Appln. No. GB1514079.1, dated May 4, 2016, 9 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
Hill, "Cannabidivarin-rich cannabis extracts are anticonvulsant in mouse and rat via a CB1 receptor-independent mechanism," British Journal of Pharmacology, Oct. 2013, 170(3): 679-692.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc.* v. *GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
Iuphar/BPS Guide to Pharmacology [online], "Entry for $\Delta 9$-tetrahydrocannabidiol," available on or before Mar. 29, 2016, retrieved on Jun. 20, 2018, URL <http://www.guidetopharmacology.org/GRAC/LigandDisplayForward?tab=biology&ligandId=242>, 2 pages.
Jones et al. [online], Info & Metrics/Article Information,"Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
[No Author Listed], Cover and Table of Contents, J Pharmacology and Exp Therapeutics, Feb. 2010, 332(2), 4 pages.
PCT International Preliminary Report on Patentability in International Appln. No. PCT/GB2015/051775, dated Aug. 10, 2016, 9 pages.
PCT International Search Report and Written Opinion in International Appln. PCT/GB2017/051943, dated Sep. 12, 2017, 10 pages.
Poortman-van der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, Apr. 2007, 68(15): 1197-1204.
Pouton, "Lipid formulations for oral administration of drugs: non-emulsifying, self-emulsifying and 'self-microemulsifying' drug delivery systems,"Eur. J Pharm Sci, Oct. 2000, 11(Supp. 2): S93-S98.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutieres syndrome," Official J Eur Paediatric Neurology Society, 2014, 18: 30-37.
Thumma et al., "Influence of plasticizers on the stability and release of a prodrug of $\Delta 9$-tetrahydrocannabinol incorporated in poly(ethylene oxide) matrices," Eur J Pharmceutics and Biopharmaceutics, Oct. 2008, 70(2): 605-614.
Unimed Pharmaceuticals, Inc., "Marinol®," Jul. 2006 <https://www.accessdata.fda.gov/drugsatfda_docs/label/2006/018651s025s0261b1.pdf>, 11 pages.
USPTO Information Disclosure Statement Form PTO-1449 in U.S. Appl. No. 13/380,305, dated Nov. 24, 2014, 8 pages.
Zhornitsky and Potvin, "Cannabidiol in Humans—The Quest for Therapeutic Targets," Pharmaceuticals, 2012, 5:529-552.

\* cited by examiner

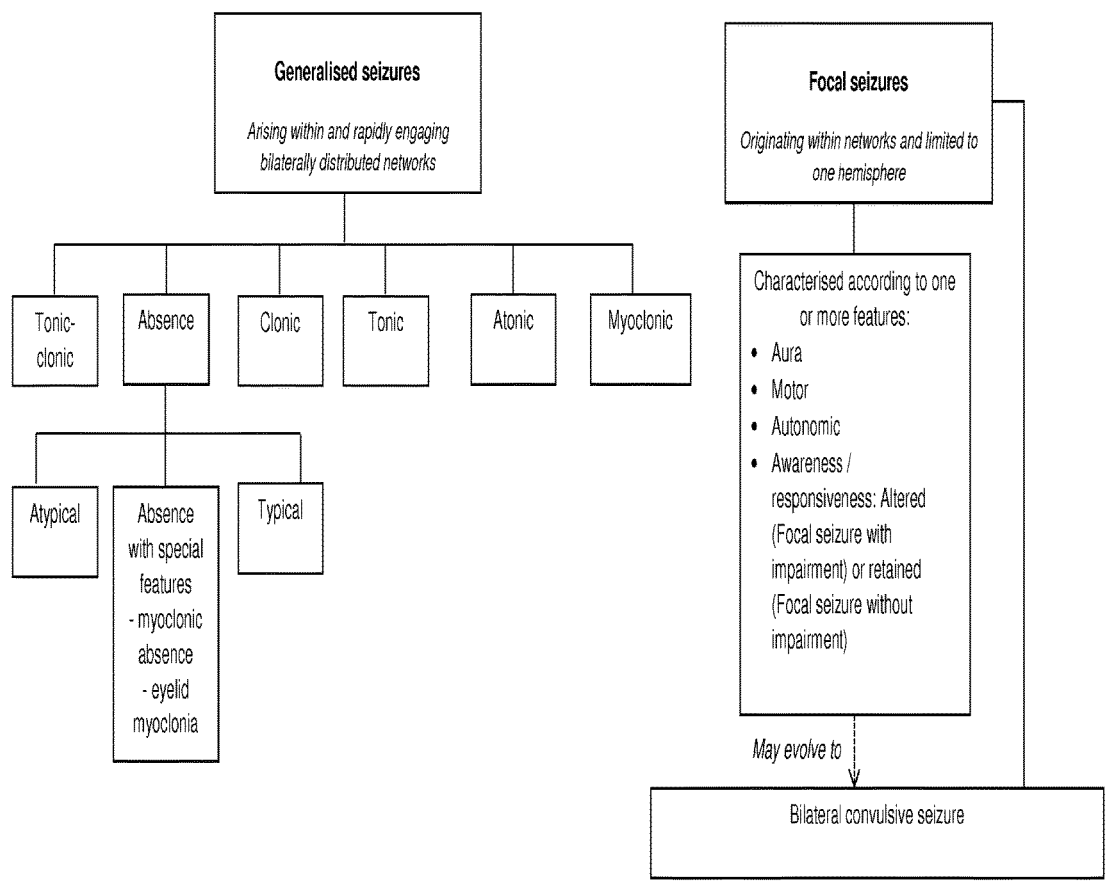

USE OF CANNABINOIDS IN THE TREATMENT OF EPILEPSY

RELATED APPLICATION

This application is a continuation of Ser. No. 14/881,969, filed Oct. 13, 2015, which claims priority to GB 1418171.3, filed Oct. 14, 2014, each of which is incorporated herein by reference in its entirety.

FIELD OF THE INVENTION

The present invention relates to the use of cannabidiol (CBD) in the treatment of atonic seizures. In one embodiment the patients suffering from atonic seizures are children and young adults. CBD appears particularly effective in reducing atonic seizures in patients suffering with etiologies that include: Lennox-Gastaut Syndrome; Tuberous Sclerosis Complex; Dravet Syndrome; Doose Syndrome; Aicardi syndrome; CDKL5 and Dup15q in comparison to other seizure types.

In these patients treatment with CBD reduced the occurrence of atonic seizures by greater than 50% in a large proportion, namely 63%, of patients. This was surprising given that the proportion of patients benefitting from a greater than 50% reduction in total seizures was significantly less, (46%), in all subjects treated.

Preferably the CBD used is in the form of a highly purified extract of cannabis such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD may be given concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as *"failure of adequate trials of two tolerated and appropriately chosen and used AED schedules (whether as monotherapies or in combination) to achieve sustained seizure freedom"* (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal. In addition the term "simple partial seizure" has been replaced by the term "focal seizure where awareness/responsiveness is not impaired" and the term "complex partial seizure" has been replaced by the term "focal seizure where awareness/consciousness is impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace Secondary Generalized Seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Atonic seizures involve the loss of muscle tone, causing the person to fall to the ground. These are sometimes called 'drop attacks' and are usually brief (less than 15 seconds). Atonic seizures can occur without warning while standing, sitting and walking and the patient often suffers from trauma due to falling.

Atonic seizures are often associated with Lennox-Gastaut Syndrome but also occur, and may be symptomatic of other types of epileptic syndromes including: Tuberous Sclerosis Complex; Dravet Syndrome; Doose Syndrome; Aicardi syndrome; CDKL5 and Dup15q.

Epileptic syndromes often present with many different types of seizure and identifying the types of seizure that a patient is suffering from is important as many of the standard AED's are targeted to treat or are only effective against a given seizure type/sub-type.

One such childhood epilepsy syndrome is Lennox-Gastaut syndrome. Lennox-Gastaut syndrome is a severe form of epilepsy. Seizures usually begin before the age of 4. Seizure types, which vary among patients, include tonic (stiffening of the body, upward deviation of the eyes, dilation of the pupils, and altered respiratory patterns), atonic (brief loss of muscle tone and consciousness, causing abrupt falls), atypical absence (staring spells), and myoclonic (sudden muscle jerks). There may be periods of frequent seizures mixed with brief, relatively seizure-free periods.

Most children with Lennox-Gastaut syndrome experience some degree of impaired intellectual functioning or information processing, along with developmental delays, and behavioural disturbances.

Lennox-Gastaut syndrome can be caused by brain malformations, perinatal asphyxia, severe head injury, central nervous system infection and inherited degenerative or metabolic conditions. In 30-35 percent of cases, no cause can be found.

The first line treatment for atonic seizures, including the treatment of atonic seizures in patients with Lennox-Gastaut syndrome usually comprises a broad spectrum AED, such as sodium valproate often in combination with lamotrigine. Other AED that may be considered include rufinamide, felbamate, clobazam and topiramate.

AED such as carbamezapine, gabapentin, oxcarbazepine, pregabalin, tiagabineor and vigabatrin are contra-indicated in atonic seizures.

Common AED defined by their mechanisms of action are described in the following tables:

TABLE 1

Examples of narrow spectrum AED

| Narrow-spectrum AED | Mechanism | Indication |
|---|---|---|
| Phenytoin | Sodium channel | Complex partial<br>Tonic-clonic |
| Phenobarbital | GABA/Calcium channel | Partial seizures<br>Tonic-clonic |
| Carbamazepine | Sodium channel | Partial seizures<br>Tonic-clonic<br>Mixed seizures |
| Oxcarbazepine | Sodium channel | Partial seizures<br>Tonic-clonic<br>Mixed seizures |
| Gabapentin | Calcium channel | Partial seizures<br>Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures<br>Partial seizures<br>Infantile spasms due to West syndrome |

TABLE 2

Examples of broad spectrum AED

| Broad-spectrum AED | Mechanism | Indication |
|---|---|---|
| Valproic acid | GABA/Sodium channel | First-line treatment for tonic-clonic seizures, absence seizures and myoclonic seizures |

TABLE 2-continued

Examples of broad spectrum AED

| Broad-spectrum AED | Mechanism | Indication |
|---|---|---|
| Lamotrigine | Sodium channel | Second-line treatment for partial seizures and infantile spasms.<br>Intravenous use in status epilepticus<br>Partial seizures<br>Tonic-clonic<br>Seizures associated with Lennox-Gastaut syndrome |
| Topiramate | GABA/Sodium channel | Seizures associated with Lennox-Gastaut syndrome |
| Zonisamide | GABA/Calcium/Sodium channel | Adjunctive therapy in adults with partial-onset seizures<br>Infantile spasm<br>Mixed seizure<br>Lennox-Gastaut syndrome<br>Myoclonic<br>Generalised tonic-clonic seizure |
| Levetiracetam | Calcium channel | Partial seizures<br>Adjunctive therapy for partial, myoclonic and tonic-clonic seizures |
| Clonazepam | GABA | Typical and atypical absences<br>Infantile myoclonic<br>Myoclonic seizures<br>Akinetic seizures<br>Atonic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
|---|---|---|
| Clobazam | GABA | Adjunctive therapy in complex partial seizures<br>Status epilepticus<br>Myoclonic<br>Myoclonic-absent<br>Simple partial<br>Complex partial<br>Absence seizures<br>Lennox-Gastaut syndrome |
| Stiripentol | GABA | Severe myoclonic epilepsy in infancy (Dravet syndrome) |

From these tables it can be seen that there is only one drug currently approved for use in the treatment of atonic seizures, namely clonazepam. This medication works by the GABA mechanism.

Over the past forty years there have been a number of animal and human studies on the use of the non-psychoactive cannabinoid cannabidiol (CBD) to treat seizures.

A study in 1978 provided 200 mg/day of pure CBD to four adult patients, two of the four patients became seizure free, whereas in the remainder, seizure frequency was unchanged (Mechoulam and Carlini, 1978).

Cunha et al. reported that administration of CBD to eight adult patients with generalized epilepsy resulted in a marked reduction of seizures in 4 of the patients (Cunha et al., 1980) and Consroe et al., (1982) determined that CBD was able to prevent seizures in mice after administration of pro-convulsant drugs or an electric current.

In contrast to the studies described above, an open label study reported that 200 mg/day of pure CBD was ineffective in controlling seizures in twelve institutionalized adult patients (Ames and Cridland, 1986).

All of the studies described above focused on the treating subjects suffering from generalised epilepsy and did not look at the treatment of specific seizure sub-types.

More recently, WO 2011/001169 describes the use of CBD in the treatment of focal seizures, WO 2012/093255 describes the use of CBD in combination with standard anti-epileptic drugs in the treatment of epilepsy and WO 2013/045891 describes a composition comprising CBD and CBDV for use in the treatment of epilepsy.

In November 2013 the company GW Pharmaceuticals made a press release to state that they were intending to treat Dravet Syndrome with CBD as it had received orphan drug designation. The company made a further press release in February 2014 that that they were intending to treat Lennox-Gastaut Syndrome with CBD as it had also received orphan drug designation.

Again the rationale was to treat a disease as opposed to the type of seizure that the subject experienced.

It has additionally been suggested that cannabis which is enriched in CBD may be efficacious in the treatment of epilepsy. A case study of a child with Lennox-Gastaut syndrome showed improvement in seizure frequency after treatment with CBD in an oily solution was reported in 2005 (Pelliccia et al. 2005).

Porter and Jacobson (2013) report on a parent survey conducted via a Facebook group which explored the use of cannabis which was enriched with CBD in children with treatment-resistant epilepsy. It was found that sixteen of the 19 parents surveyed reported an improvement in their child's epilepsy. The children surveyed for this paper were all taking cannabis that was purported to contain CBD in a high concentration although the amount of CBD present and the other constituents including THC were not known for many of the cases. Indeed, whilst CBD levels ranged from 0.5 to 28.6 mg/kg/day (in those extracts tested), THC levels as high as 0.8 mg/kg/day were reported. Providing children with TRE with a cannabis extract that comprises THC, which has been described as a pro-convulsant (Consroe et al., 1977), at a potentially psychoactive dose of 0.8 mg/kg/day, is a concern.

In addition a paper published in June 2014 describes the use of a high-CBD strain to treat a patient with Dravet Syndrome; the patient's seizure frequency was stated to be reduced by the treatment (Maa et al. 2014).

A document published after the priority application was filed discloses the use of CBD in the treatment of refractory epilepsy in the treatment of Tuberous Sclerosis Complex in patients having focal onset seizures (Geffrey et al., 2014).

Whilst the potential of cannabis and the cannabinoids, including CBD, to treat epilepsy has been rekindled, to date there has been little in the way of real data to support its efficacy in patients.

The applicant has found that CBD shows significant efficacy in reducing atonic seizures, by greater than 50% in a large proportion, namely 63%, of patients. By way of comparison the proportion of patients benefitting from a greater than 50% reduction in total seizures was significantly less, (46%), in all subjects treated.

It is additionally worth noting that the patients being treated were treatment resistant to existing AED and so consequently these figures are even the more remarkable.

BRIEF SUMMARY OF THE DISCLOSURE

In accordance with a first aspect of the present invention there is provided cannabidiol (CBD) for use in the treatment of atonic seizures.

Preferably the atonic seizures are treatment-resistant.

Preferably the atonic seizures associated with Lennox-Gastaut Syndrome; Tuberous Sclerosis Complex; Dravet Syndrome; Doose Syndrome; Aicardi syndrome, CDKL5 or Dup15q.

In one embodiment the CBD is for use in combination with one or more concomitant anti-epileptic drugs (AED).

In a further embodiment the CBD is present as a highly purified extract of cannabis which comprises at least 95% (w/w) CBD, more preferably 98% (w/w) CBD. Preferably the extract comprises less than 0.15% THC. More preferably the extract further comprises up to 1% CBDV.

In an alternative embodiment the wherein the CBD is present as a synthetic compound.

In a further embodiment of the invention the one or more AED is selected from the group consisting of: clobazam; clonazepam, levetiracetam; topiramate; stiripentol; phenobarbital; lacsamide; valproic acid; zonisamide; perampanel; and fosphenytoin.

Preferably the number of different anti-epileptic drugs that are used in combination with the CBD is reduced. Alternatively the dose of the one or more anti-epileptic drugs that are used in combination with the CBD is reduced.

Preferably the dose of CBD is greater than 5 mg/kg/day.

In accordance with a second aspect of the present invention there is provided a method of treating atonic seizures comprising administering cannabidiol (CBD) to a subject.

In accordance with a third aspect of the present invention there is provided a composition for use in the treatment of atonic seizures characterised by atonic seizures comprising cannabidiol (CBD), a solvent, a co-solvent, a sweetener, and a flavouring.

Preferably the solvent is sesame oil, the co-solvent is ethanol, the sweetener is sucralose, the flavouring is strawberry flavour and the CBD is present at a concentration of between 25 mg/ml and 100 mg/ml.

More preferably the composition comprises cannabidiol (CBD) at a concentration of between 25 to 100 mg/ml, ethanol at a concentration of 79 mg/ml, sucralose at a concentration of 0.5 mg/ml, strawberry flavouring at a concentration of 0.2 mg/ml and sesame q.s. to 1.0 ml.

BRIEF DESCRIPTION OF THE DRAWINGS

FIG. 1 shows the ILEA 2010 proposal for revised terminology for organization of seizures and epilepsies.

DEFINITIONS

Definitions of some of the terms used to describe the invention are detailed below:

The cannabinoids described in the present application are listed below along with their standard abbreviations.

TABLE 4

| Cannabinoids and their abbreviations | | |
|---|---|---|
| CBD | Cannabidiol | *(structure)* |
| CBDA | Cannabidiolic acid | *(structure)* |
| CBDV | Cannabidivarin | *(structure)* |
| CBDVA | Cannabidivarinic acid | *(structure)* |
| THC | Tetrahydrocannabinol | *(structure)* |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

"Atonic Seizures" are defined as a convulsive type of epileptic seizure which causes the muscles to relax and the patient to flop or fall.

"Mixed seizures" are defined as the existence of both generalised and focal seizures in the same patient.

The terms "50% responder" and "50% reduction in seizure" are both terms used in clinical studies. In the present application the terms define the percentage of subjects that experienced a greater than or equal to 50% reduction in the number of seizures during treatment with CBD in comparison to the number experienced during the baseline period before the CBD was administered.

DETAILED DESCRIPTION

Preparation of Highly Purified CBD Extract

The following describes the production of the highly-purified (>98% w/w) cannabidiol extract which has a known and constant composition which was used for the expanded access trials described in Examples below.

In summary the drug substance used in the trials is a liquid carbon dioxide extract of high-CBD containing chemotypes of Cannabis sativa L. which had been further purified by a solvent crystallization method to yield CBD. The crystallisation process specifically removes other cannabinoids and plant components to yield greater than 95% CBD w/w, typically greater than 98% w/w.

The Cannabis sativa L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 5 below.

TABLE 5

| CBD Specification | | |
|---|---|---|
| Test | Test Method | Limits |
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |

TABLE 5-continued

| CBD Specification | | |
|---|---|---|
| Test | Test Method | Limits |
| Total Purity | Calculation | ≥98.0% |
| Chromatographic Purity 1 | HPLC-UV | ≥98.0% |
| Chromatographic Purity 2 | GC-FID/MS | ≥98.0% |
| Other Cannabinoids: | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT—Not more than

The purity of the CBD drug substance achieved is greater than 98%. The other cannabinoids which may occur in the extract are: CBDA, CBDV, CBD-C4 and THC.

Distinct chemotypes of Cannabis sativa L. plant have been produced to maximize the output of the specific chemical constituents, the cannabinoids. One type of plant produces predominantly CBD. Only the (−)-trans isomer occurs naturally, furthermore during purification the stereochemistry of CBD is not affected.

Production of the Intermediate

An overview of the steps to produce a botanical extract, the intermediate, are as follows:

1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS) which was used for crystallisation to produce the test material.

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS.

Production of the Drug Substance

The manufacturing steps to produce the drug substance from the intermediate botanical extract are as follows:

1. Crystallization using C5-C12 straight chain or branched alkane
2. Filtration

3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 liter stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis.

The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sucralose and flavouring. Two product strengths are available to allow dose titration across a wide dose range.

The 25 mg/ml solution is appropriate at lower doses and the 100 mg/ml solution at higher doses.

The drug product formulation is as described in Table 6 below:

TABLE 6

Drug Product specification

| Component | Qualitative Composition | Function | Reference to Quality Standard |
|---|---|---|---|
| Cannabidiol (CBD) | 25 mg/ml or 100 mg/ml | Active | In-house |
| Anhydrous ethanol | 79.0 mg/ml* | Excipient | Ph.Eur. |
| Sucralose | 0.5 mg/ml | Sweetener | In-house |
| Strawberry flavouring | 0.2 mg/ml | Flavouring | In-house |
| Sesame oil | q.s to 1.0 ml | Excipient | Ph.Eur. |

The drug substance, CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 6 by an amount of up to 10%.

Example 1 below describes the use of a highly purified cannabis extract comprising cannabidiol (CBD) in an expanded access treatment program in children with TRE.

Example 1: Efficacy of Cannabidiol Reducing Atonic Seizures in Children and Young Adults with Intractable Epilepsy Materials and Methods Of 137 children and young adults with severe, childhood onset treatment-resistant epilepsy (TRE), twenty-seven suffered from epilepsy that was characterised by atonic seizures. These subjects were tested with a highly purified extract of cannabidiol (CBD) obtained from a cannabis plant. All subjects presented with atonic type seizures, often in addition to other seizures. The participants in the study were part of an expanded access compassionate use program for CBD.

The epileptic syndromes that these patients suffered from were as follows: Lennox-Gastaut Syndrome; Tuberous Sclerosis Complex; Dravet Syndrome; Doose Syndrome; Aicardi syndrome, CDKL5 and Dup15q.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after 4 weeks of CBD therapy.

All patients were taking at least two concomitant anti-epileptic drugs. These included clobazam; levetiracetam; topiramate; stiripentol; phenobarbital; lacsamide; valproic acid; zonisamide. The average number of concomitant anti-epileptic drugs being taken was 2.7. The majority took either clobazam and/or valproic acid.

Results

There were 27 children and young adult patients all of whom suffered from atonic seizures received treatment with CBD for at least 12 weeks.

A summary of the 50% responders, based on 12 weeks of treatment are summarized in Table 7 below.

TABLE 7

Summary of 50% responders after 12 weeks of treatment for atonic seizures

| | Atonic seizures (n = 27) | Total seizures (n = 137) |
|---|---|---|
| >50% reduction in seizures | 63% (n = 17) | 46% (n = 63) |
| <50% reduction in seizures | 37% (n = 10) | 54% (n = 74) |

Table 7 shows that after 3 months of therapy, a remarkable 63% of patients had an equal to or greater than >50% reduction in atonic seizures, these data infer that the CBD is very effective at reducing this type of seizure.

CONCLUSIONS

These data indicate that CBD significantly reduces the number of atonic seizures in a high proportion of patients that do not respond well to existing AED.

It was surprising that in this group of patients which are treatment-resistant such a high number were able to gain an effect. The fact that nearly two thirds of the patients (63%) benefitted from at least a fifty percent reduction in the number of atonic seizures that they suffered from was remarkable.

Furthermore when these data are compared to the other sub-types of generalised seizure, it can clearly be seen that CBD was able to selectively reduce the occurrence of atonic seizures. Table 8 below details these findings.

TABLE 8

Summary of 50% responders after 12 weeks of treatment for all seizure sub-types

| | Atonic seizures (n = 27) | Tonic seizures (n = 45) | Tonic-clonic seizures (n = 65) | Clonic seizures (n = 8) | Myoclonic seizures (n = 30) | Absence seizures (n = 28) |
|---|---|---|---|---|---|---|
| >50% reduction in seizures | 63% (n = 17) | 49% (n = 22) | 43% (n = 28) | 50% (n = 4) | 43% (n = 13) | 64% (n = 18) |
| <50% reduction in seizures | 37% (n = 10) | 51% (n = 23) | 37% (n = 37) | 50% (n = 4) | 57% (n = 17) | 36% (n = 10) |

From Table 8 it can be seen that when the number of atonic seizures recorded is compared with other generalised seizure types such as tonic seizures (49% of patients experienced a greater than 50% reduction in seizure), tonic-clonic seizures (43% of patients experienced a greater than 50% reduction in seizure), and myoclonic seizures (43% of patients experienced a greater than 50% reduction in seizure) the fact that nearly two thirds (63%) of patients experiencing atonic seizures had a greater than 50% reduction in the number of seizures that occurred is very surprising.

REFERENCES

Ames F R and Cridland S (1986). "Anticonvulsant effects of cannabidiol." S Afr Med J 69:14.

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85

Dravet C. The core Dravet syndrome phenotype. Epilepsia. 2011 April; 52 Suppl 2:3-9.

Eadie, M J (December 2012). "Shortcomings in the current treatment of epilepsy." *Expert Review of Neurotherapeutics* 12 (12): 1419-27.

Geffrey A, Pollack S, Paolini J, Bruno P, Thiele E (2014) "Cannabidiol (CBD) treatment for refractory epilepsy in Tuberous Sclerosis Complex (TSC)." American Epilepsy Society Annual Meeting. 5-9 December 2014.

Kwan P, Arzimanoglou A, Berg A T, Brodie M J, Hauser W A, Mathern G, Moshé S L, Perucca E, Wiebe S, French J. (2009) "Definition of drug resistant epilepsy: Consensus proposal by the ad hoc Task Force of the ILAE Commission on Therapeutic Strategies." *Epilepsia*.

Maa E and Figi P (2014). "The case for medical marijuana in epilepsy", Epilepsia 55(6):783-786

Mechoulam R and Carlini E A (1978). "Toward drugs derived from cannabis." Die naturwissenschaften 65:174-9.

Pelliccia A, Grassi G, Romano A, Crocchialo P (2005). "Treatment with CBD in oily solution of drug resistant paediatric epilepsies". Congress of Cannabis and the Cannabinoids, Leiden, The Netherlands. International Association for Cannabis as a Medicine. p 14.

Porter B E, Jacobson C (December 2013). "Report of a parent survey of cannabidiol-enriched cannabis use in paediatric treatment resistant epilepsy" Epilepsy Behaviour. 29(3) 574-7

Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." *Epilepsia*. 52 Suppl 7: 2-26

The invention claimed is:

1. A method of reducing drop seizure frequency in a patient with Lennox-Gastaut syndrome, comprising administering to the patient in need thereof cannabidiol (CBD), wherein the CBD has a purity of at least 98% (w/w) CBD and comprises not more than 0.15% (w/w) Δ9-tetrahydrocannabinol (THC); and wherein the dose of the CBD is about 20 mg/kg/day.

2. The method of claim 1, wherein the CBD is administered in combination with one or more concomitant antiepileptic drugs (AED) to the subject in need thereof at a recommended therapeutic dose of the AED.

3. The method of claim 1, wherein the one or more AED is selected from the group consisting of: clobazam; clonazepam, levetiracetam; topiramate; stiripentol; phenobarbital; lacsamide; valproic acid; zonisamide; perampanel; and fosphenytoin.

4. A method of reducing drop seizure frequency in a patient with Lennox-Gastaut syndrome, comprising administering to the patient in need thereof cannabidiol (CBD) and clobazam, wherein the CBD has a purity of at least 98% (w/w) CBD and comprises not more than 0.15% (w/w) Δ9-tetrahydrocannabinol (THC); and wherein the dose of the CBD is about 20 mg/kg/day.

5. A method of treating drop seizures in a patient with Lennox-Gastaut syndrome, comprising administering to the patient in need thereof cannabidiol (CBD), wherein the CBD has a purity of at least 98% (w/w) CBD and comprises not more than 0.15% (w/w) Δ9-tetrahydrocannabinol (THC); and wherein the dose of the CBD is about 20 mg/kg/day.

6. The method of claim 5, wherein the CBD is administered in combination with one or more concomitant antiepileptic drugs (AED) to the subject in need thereof at a recommended therapeutic dose of the AED.

7. The method of claim 5, wherein the one or more AED is selected from the group consisting of: clobazam; clonazepam, levetiracetam; topiramate; stiripentol; phenobarbital; lacsamide; valproic acid; zonisamide; perampanel; and fosphenytoin.

8. A method of treating drop seizures in a patient with Lennox-Gastaut syndrome, comprising administering to the patient in need thereof cannabidiol (CBD) and clobazam, wherein the CBD has a purity of at least 98% (w/w) CBD and comprises not more than 0.15% (w/w) Δ9-tetrahydrocannabinol (THC); and wherein the dose of the CBD is about 20 mg/kg/day.

* * * * *

UNITED STATES PATENT AND TRADEMARK OFFICE
CERTIFICATE OF CORRECTION

PATENT NO. : 10,137,095 B2
APPLICATION NO. : 15/449535
DATED : November 27, 2018
INVENTOR(S) : Geoffrey Guy et al.

Page 1 of 1

It is certified that error appears in the above-identified patent and that said Letters Patent is hereby corrected as shown below:

In the Claims

Column 14, Line 34, in Claim 3, delete "lacsamide;" and insert -- lacosamide; --.

Column 14, Line 56, in Claim 7, delete "lacsamide;" and insert -- lacosamide; --.

Signed and Sealed this
Twenty-eighth Day of May, 2019

Andrei Iancu
*Director of the United States Patent and Trademark Office*

UNITED STATES PATENT AND TRADEMARK OFFICE
CERTIFICATE OF CORRECTION

PATENT NO. : 10,137,095 B2
APPLICATION NO. : 15/449535
DATED : November 27, 2018
INVENTOR(S) : Guy et al.

Page 1 of 1

It is certified that error appears in the above-identified patent and that said Letters Patent is hereby corrected as shown below:

On the Title Page

Item (73) Assignee:
"GW Pharma Limited, Cambridge, (GB)"
Should read:
--GW Research Limited, Cambridge, (GB)--.

In the Claims

Claim 2 Column 14, Line 29:
"subject"
Should read:
--patient--.

Claim 6 Column 14, Line 51:
"subject"
Should read:
--patient--.

Signed and Sealed this
Fifth Day of May, 2020

Andrei Iancu
*Director of the United States Patent and Trademark Office*